United States Patent [19]

Yokomichi et al.

[11] Patent Number: 5,128,251
[45] Date of Patent: Jul. 7, 1992

[54] IMMOBILIZED LIPOLYTIC ENZYME FOR ESTERIFICATION AND INTERESTERIFICATION

[75] Inventors: Hideki Yokomichi; Takeshi Yasumasu; Kazuhiro Nakamura, all of Ibaraki; Yoshiharu Kawahara, Chiba, all of Japan

[73] Assignee: Kao Corporation, Tokyo, Japan

[21] Appl. No.: 685,158

[22] Filed: Apr. 12, 1991

Related U.S. Application Data

[63] Continuation of Ser. No. 276,374, Nov. 23, 1988, abandoned.

[30] Foreign Application Priority Data

Dec. 9, 1987 [JP] Japan ............................ 62-311549
Dec. 9, 1987 [JP] Japan ............................ 63-311550
Dec. 9, 1987 [JP] Japan ............................ 62-311551
Dec. 28, 1987 [JP] Japan ............................ 62-335854

[51] Int. Cl.$^5$ .................... C12P 7/64; C12P 7/62; C12N 11/08
[52] U.S. Cl. ........................ 435/134; 435/135; 435/177; 435/180; 435/198; 435/939
[58] Field of Search ............... 435/134, 135, 174, 177, 435/178, 179, 180, 198, 939

[56] References Cited

U.S. PATENT DOCUMENTS

| | | | |
|---|---|---|---|
| 3,798,793 | 1/1974 | Eigtved | 435/134 |
| 3,909,360 | 9/1975 | Horiuchi et al. | 435/178 |
| 4,472,503 | 9/1984 | Matsuo et al. | 435/176 |
| 4,818,695 | 4/1989 | Eigtved | 435/134 |

FOREIGN PATENT DOCUMENTS

| | | | |
|---|---|---|---|
| 0126416 | 11/1984 | European Pat. Off. | |
| 0028483 | 2/1984 | Japan | 435/134 |
| 61-187795 | 8/1986 | Japan | |
| 62-134090 | 6/1987 | Japan | |
| 2159527 | 12/1985 | United Kingdom | |
| 2168983 | 7/1986 | United Kingdom | |

OTHER PUBLICATIONS

Chemical Abstracts, vol. 102, No. 11, 1985, p. 470, No. 94351q.
Chemical Abstracts, vol. 107, No. 13, 1987, p. 293, No. 111803m.
"Application of Immobilized Lipase to Hydrolysis of Triaglyceride", Eur. J. App. Microbiol Biotechnol (1983), 17: 107-112.
"Purification and Some Properties of Cell-bound Lipase from *Saccharomycopsis lipolytica*", Agric. Biol. Chem. 46, (12) pp. 2885-2893, 1982.
"Isolation and Identification of Lipase Activators from *Saccharomycopsis lipolytica*", Agric. Biol. Chem. 50, (10) pp. 2525-2530, 1986.
"Lipase-Catalyzed Interesterification of Oils and Fats", JAOCS, vol. 60. No. 2, pp. 243A-246A., 1983.

Primary Examiner—David M. Naff
Attorney, Agent, or Firm—Flynn, Thiel, Boutell & Tanis

[57] ABSTRACT

An immobilized lipolytic enzyme for esterification and interesterification of fats and oils is prepared by adsorbing a fatty acid or a derivative thereof onto an insoluble carrier and then adsorbing a lipolytic enzyme onto the carrier in an aqueous medium. The resultant immobilized lipolytic enzyme can be dried to a water content of 2 wt. % or less. Preferably, the carrier is a phenol/formaldehyde resin, the lipolytic enzyme is from *Rhizopus japonicus* and the fatty acid is linoleic acid, lauric acid, stearic acid, ricinoleic acid or isostearic acid. A reaction column can be charged with the dried immobilized lipolytic enzyme and reaction continuously carried out without the use of a solvent. Preferably, starting materials have a water content of 0.01 to 0.2 wt. % and residence time in the column is 2 hours or shorter.

13 Claims, No Drawings

IMMOBILIZED LIPOLYTIC ENZYME FOR ESTERIFICATION AND INTERESTERIFICATION

This application is a continuation of U.S. Pat. Ser. No. 07/276,374, filed Nov. 23, 1988, now abandoned.

This invention relates to an immobilized enzyme prepared from a lipid-decomposing enzyme such as a lipase, phospholipase or cholesterol esterase, which will be sometimes simply called an enzyme hereinafter, suitable for the formation of an ester bond and for transesterification as well as to an esterification process using said immobilized enzyme.

PRIOR ART

Esterification is highly important in the preparation of various products, for example, wax esters prepared by reacting a monohydric aliphatic alcohol with a fatty acid; esters such as monoglycerides, polyglycerol fatty acid esters or sugar esters prepared by reacting a polyhydric alcohol with a fatty acid; steroid esters such as cholesteryl palmitate and terpene alcohol esters such as geranyl butyrate.

A base exchange reaction of phospholipids, which is generally known as transphosphatidylation, is also important in the preparation of, for example, useful physiologically active substances.

Lipase, which is a lipid-decomposing enzyme, is applied to the synthesis of fats and esters as well as to exchange reactions thereof, since it reacts under mild conditions and has specific properties such as site-selectivity and alkyl-selectivity. However these reactions can proceed only in a system of a limited moisture content, different from hydrolysis in which the lipase inherently participates. On the other hand, a small amount of moisture is required for an enzyme in order to enhance the esterifying and transesterifying activities of the lipase. A reaction in a low moisture content system, as disclosed in Japanese Patent Laid-Open No. 71797/1980, suffers from such disadvantages that no sufficient reaction rate can be achieved and that a supply of an excessive amount of moisture, in order to elevate the reaction rate, would cause a preferential increase the decomposition of an ester. Japanese Patent Laid-Open No. 19495/1985 and No. 203196/1985 have each proposed a two-stage process comprising a decomposition stage in a high moisture content system and a synthesis stage wherein the moisture is removed. However the synthesis reaction rate in the latter stage is insufficient, compared with the transesterification rate in a common process. Further, this two-stage process unavoidably requires troublesome procedures.

In order to overcome these problems and to efficiently utilize the lipase, there have been attempts to immobilize this enzyme. It is expected that the immobilization of the lipase might bring about the following advantages. When the lipase is used in the form of an aqueous solution, it can hardly be mixed or dispersed in an oil homogeneously. In contrast thereto, lipase immobilized on an insoluble carrier can be easily dispersed in an oil. Further, a small amount of moisture can be held in the insoluble carrier. Thus, esterification or transesterification can be readily carried out in a low moisture content system in the latter case. In addition, the immobilized lipase, which is an expensive catalyst, can be readily recovered and reused. The immobilized lipase is further advantageous from the viewpoint of esterification or transesterification on an industrial scale, since it enables continuous operation.

Although an immobilized enzyme is highly advantageous as described above, it is still impossible at present to simultaneously achieve both the maintenance of the moisture content required for the enhancement of the esterifying activity of lipase and the suppression of a reverse reaction, i.e., hydrolysis.

For example, it has been pointed out that the addition of a trace amount of water would accelerate the hydrolysis (cf. J. Amer. Oil Chem. Soc., 60, 291-294 (1983)). When the water is substituted with a polyhydric alcohol such as glycerol, the hydrolysis is somewhat suppressed but the esterification or transesterification rate is lowered thereby. Japanese Patent Laid-Open No. 213390/1984 has proposed a process with the use of a carrier capable of holding moisture required by an enzyme which is obtained by coating a resin of a high water absorption capability, i.e., a porous carrier with chitosan and then grinding the same. This process also comprises two stages in order to achieve both the esterification or transesterification of the immobilized enzyme and the decomposition of the same (cf. Japanese Patent Laid-Open No. 203196/1985). Japanese Patent Laid-Open No. 98984/1985 and No. 202688/1986 have both disclosed an immobilized enzyme which is thermally stable and thus is available in transesterification or esterification up to 80° C. However enzymatic and nonenzymatic rearrangements of diglycerides from 1,2-form to 1,3-form would rapidly proceed within a temperature range of 60° to 80° C. characteristic to the above immobilized enzyme. Thus it has been required to develop an immobilized enzyme showing a higher transesterification rate in order to prepare a symmetric fat containing an oleic acid residue at the 2-position of a glyceride, similar to cacao fat.

As described above, it has been urgently required in esterification or transesterification to control the moisture content in the reaction system or to developan immobilized enzyme having an elevated esterifying or transesterifying activity.

Regarding esterification, the lipase is used in the form of an aqueous solution in most conventional methods. In these cases, the decomposition/synthesis equilibrium goes far to the decomposition reaction, which gives a low yield of the aimed ester (cf. Japanese Patent Publication B No. 7754/1976 and No. 187795/1986). When an immobilized enzyme is employed, the esterification can be effected in a low moisture content system and the used enzyme can be readily recovered. In this case, however, it is also required to develop an immobilized enzyme of an elevated activity in order to attain a reaction rate comparable to those of common chemical processes.

Known methods for elevating the esterifying and transesterifying activities of lipases include the addition of a fat to a lipase and effecting hydrolysis to thereby immobilize the lipase in the presence of the fat and a fatty acid (cf. Japanese Patent Laid-Open No. 251884/1985); and the drying of a lipase in the presence of a fatty acid derivative (cf. Japanese Patent Laid-Open No. 134090/1987). However the immobilized lipase obtained by such a method shows insufficient esterifying and transesterifying activities to be employed on an industrial scale.

From the viewpoint of activity yield, every conventional immobilization method gives only a limited yield. Examples of these methods include one wherein lipase is immobilized by using an organic metal derivative of an ion exchange resin as a carrier (cf. Japanese Patent Laid-Open No. 87293/1977); one wherein lipase is immobilized by using a higher fatty acid ester of a polysaccharide as a carrier (cf. Japanese Patent Publication B 27787/1978); and one wherein lipase is bound to an ion exchange resin simply via an ionic bond (cf. Y. Kimura et al., Eur. J. Appl. Microbiol. Biotechnol.). Therefore it has been believed very difficult to selectively immobilize lipase in the presence of other contaminants.

SUMMARY OF THE INVENTION

Under these circumstances, the present inventors have conducted extensive studies for a factor capable of elevating the esterifying and transesterifying activities of a lipid-decomposing enzyme. As a result, they have found that the esterifying and transesterifying activities of a lipid-decomposing enzyme can be elevated when said enzyme is present together with a fatty acid or a derivative thereof. Based on this finding, they have further attempted to adsorb a fatty acid or a derivative thereof on various insoluble carrier, thus completing the present invention.

An immobilized enzyme of the invention comprises an insoluble carrier and a lipolytic or lipid-decomposing enzyme adsorbed thereon, obtained by treating the carrier with a fatty acid or a derivative thereof to conduct adsorption thereof and then adsorbing and immobilizing the enzyme on the carrier in an aqueous medium and is effectively useful for esterification and interesterification of fats and oils.

It is preferable that the enzyme is selected from the group consisting of lipase, phospholipase, cholesterol esterase and sphingomyelinase and the carrier is macroporous.

The invention provides a process for producing an ester from a lower mono- or polyhydric alcohol and a higher fatty acid in the presence of the immobilized enzyme as defined above and then a process for interesterification of fats and oils in the presence of the immobilized enzyme as defined above.

In a preferable process for interesterification, the enzyme is lipase, the immobilized enzyme is dried so as to have a water content of 2 wt. % or below, a reaction column is charged with the resulting immobilized enzyme and the reaction is continuously carried out without the use of a solvent. More preferably, the starting materials have a water content of 0.01 to 0.2 wt. % and a residence time in the reaction column of 2 hours or less on the average.

In preparation of the above defined immobilized enzyme, the immobilization is conducted by mixing a water-insoluble volatile organic solvent with the carrier, separately dispersing or dissolving the enzyme in an aqueous medium, adding the enzyme to the mixture of the solvent and the carrier, then separating the carrier from the mixture and drying the carrier having the immobilized enzyme thereon until its water content reaches 5 wt. % or below.

The invention moreover provides an immobilized enzyme comprising an insoluble carrier and a lipid-decomposing enzyme adsorbed on the carrier in the presence of an oil-soluble compound selected from the group consisting of alcohols, ethers, carbonyl compounds and alkyl halides.

Accordingly the present invention relates to an immobilized enzyme having high esterifying and transesterifying activities which is obtained by adsorbing and immobilizing a lipid-decomposing enzyme on an insoluble carrier, on which a fatty acid or a derivative thereof has been preliminarily adsorbed, in an aqueous medium.

Regarding the relationship between lipase and a fatty acid or a derivative thereof, there has been merely reported that a fatty acid or a derivative thereof added to a fermentation medium would serve as an inducing substrate and that a certain unsaturated fatty acid or a derivative thereof would activate the decomposing effect of a certain lipase. More particularly, it was reported that oleic acid and 3,5-dihydroxy-7-tetradecenoic acid would activate the decomposing effect of *Saccharomyces lipotica* lipase (cf. Agric. Biol. Chem., 46, 2885 (1982) and ibid. 50, 2523 (1986)) and that castor seed lipase is required in the manifestation of the decomposing activity of a hydroxy fatty acid derivative (ricinoleate tetramer).

Since Iwai et al. reported a relationship between lipase and a phospholipid before the Japanese Biochemical Society Meeting in 1969, a number of reports have been presented hitherto. However, these reports exclusively relate to changes in the substrate specificity in hydrolysis or to the stabilization or induction of fermentative production. Namely, there are few reports on the activation of esterification or transesterification.

In contrast to these reports, the selective adsorption and esterifying and transesterifying activities of a lipid-decomposing enzyme can be considerably elevated in the present invention wherein the lipid-decomposing enzyme is immobilized by adding an insoluble carrier, on which a fatty acid or a derivative thereof has been preliminarily adsorbed, to a solution containing said lipid-decomposing enzyme and then optionally drying.

The process of the present invention has the following advantages. A first advantage thereof resides in that the aimed enzyme can be immobilized within a short period of time at a high yield from a material containing the enzyme together with, for example, other contaminating proteins such as a culture medium.

A second advantage thereof resides in that the immobilized lipid-decomposing enzyme such as lipase, which would serve, as a matter of course, at the water/fat interface, present on the surface of the carrier, can be efficiently utilized In contrast thereto, when the lipase is used in the form of an aqueous solution, the lipase might be dispersed and equilibrated at the interface and in the aqueous solution, which makes it impossible to fully utilize the enzyme in the solution.

A third advantage thereof resides in that the lipid-decomposing enzyme can be immobilized in an activated state by preliminarily adsorbing a fatty acid or a derivative thereof on the carrier. As described above, a lipid-decomposing enzyme acting at the interface has a higher-order structure for manifesting its activity when orientated in the interface. Therefore it is important to immobilize the enzyme in such a manner that it is orientated in the interface and activated. It has been found that a fatty acid or a derivative thereof is very suitable as a water-soluble substance for establishing this highly active state and that a material which simply forms a nonpolar interface, such as hexane, cannot exert the aimed effect. The immobilized enzyme thus prepared can exert a sufficient effect even at such a low moisture content of 2% or below, different from conventional ones.

Based on these findings, the present inventors have already completed an invention wherein a lipase is contacted with an insoluble carrier in the presence of a small amount of water and a fat, thus simultaneously orientating the enzyme in the interface and immobilizing the same and applied for a patent (Japanese Patent Laid-Open No. 251884/1985). Subsequently the present inventors have further examined these facts and attempted to apply the same to the preliminary adsorption of a fatty acid or a derivative thereof on various insoluble carriers. As a result, they have succeeded in the preparation of a highly active immobilized enzyme by contacting an enzyme with the abovementioned carrier thus simultaneously activating said enzyme and immobilizing the same on said carrier at a high concentration within a short period of time, thus completing the present invention.

Now the present invention will be described in detail.

In the process of the present invention, a fatty acid or a derivative thereof is contacted with a water-insoluble carrier in water or an organic solvent to thereby adsorb the former on the latter. The insoluble carrier may be optionally filtered from the solution and dried. Then it is contacted with an aqueous solution of an enzyme or a culture medium containing an enzyme for one minute to 20 hours, preferably for 30 minutes to two hours. Then the insoluble carrier is separated by filtration from said solution and washed with water or a buffer. The immobilized enzyme thus obtained is dried. Thus the immobilized enzyme of the present invention is obtained.

Examples of the lipid-decomposing enzyme to be used in the present invention include lipase, phospholipase, cholesterol esterase, sphingomyelinase and various esterases. Among these enzymes, lipase having a high site-selectivity and originating from microbial sources such as microorganisms belonging to the genera Rhizopus, Aspergillus, Mucor, Geotrichum, showing a fatty acid specificity, Candida, showing no specificity, Pseudomonas, Penicillium and Chromobacterium and lipases originating from animals such as pancreatic lipase are recommended. Among these lipases, those originating from microorganisms belonging to the genera Rhizopus, Mucor and Chromobacterium are particularly suitable because they are highly active to an alkyl group of a moderate chain length or longer and thus the esterifying activities thereof can be easily enhanced.

Examples of the cholesterol esterase include those originating from microbial sources such as microorganisms belonging to the genus Candida. Examples of the phospholipase include those originating from plants such as cabbage, peanut, carrot or moss, as well as those originating from microbial sources such as microorganisms belonging to the genus Streptomyces.

Any insoluble carrier may be used in the present invention so long as it is insoluble in water, alcohols, various organic solvents and fats. Examples thereof include inorganic carriers such as Celite, kieselguhr, kaolinite, molecular sieves, porous glass, activated carbon, calcium carbonate and ceramics as well as organic polymers such as cellulose powder, polyvinyl alcohol, chitosan, ion exchange resins and adsorptive resins, each exerts no adverse effect on the activity of the lipase and remains chemically and physiologically stable during the operation. Those carrying a hydrophobic moiety such as a resin containing $-CH_2$ groups at a high ratio or having alkyl group(s) as a functional group are particularly preferable from the viewpoint of the adsorptivity of an enzyme and the compatibility as a substrate with a lipid. When the carrier is highly hydrophobic in particular, a high immobilization yield can be achieved by adding a salt capable of forming an antichaotropic ion, such as ammonium sulfate. The carrier may be in any form such as powder, granule, fiber or sponge. In order to facilitate the operation, it is preferable to use a porous carrier having a particle size of 400 to 1000 μm and a pore size of 100 to 1500 Å. A particularly preferable insoluble carrier is a macroporous weak anion exchange resin described in Japanese Patent Laid-Open 98984/1985. Preferable examples of the insoluble carrier which are commercially available are macroporous weak anion exchange resins such as Duolite A-568 and Duolite S-762 (each mfd. by Diamond Shamrock Chemical Co.) and adsorptive resins.

It is preferable that the fatty acid to be used in the present invention have 2 to 36, more preferably 8 to 18, carbon atoms. Examples thereof include straight-chain saturated fatty acids such as capric acid, lauric acid and myristic acid, unsaturated fatty acids such as oleic acid and linoleic acid, hydroxyl fatty acids such as ricinoleic acid and branched fatty acids such as isostearic acid.

It is preferable that the fatty acid derivative to be used in the present invention have 2 to 36, still preferably 8 to 18, carbon atoms. For example, an ester obtained from a fatty acid and a compound having hydroxyl group(s) may be employed therefor. Examples thereof include monohydric alcohol esters, polyhydric alcohol esters, phospholipids and those obtained by adding ethylene oxide to these esters. Examples of the monohydric alcohol esters include methyl esters and ethyl esters while examples of the polyhydric alcohol esters include monoglycerides, diglycerides and derivatives thereof, fatty acid esters of polyhydric alcohols such as polyglycerol, sorbitan fatty acid esters and sucrose fatty acid esters.

Examples of the phospholipid to be used in the present invention include crude and purified esters such as commercially available soybean lecithin and yolk lecithin as well as purified mixtures thereof. In addition, phosphatidylcholine, phosphatidylserine, phosphatidylethanolamine, phosphatidylinositol, phospatidic acid or cardiolipin, each obtained by fractionating the abovementioned phospholipids, or a mixture thereof may be employed. Furthermore, synthetic phospholipids prepared by various methods and derivatives thereof may be employed therefor.

It is preferable from the viewpoint of operation that the fatty acid or a derivative thereof is liquid at room temperature, though the present invention is not restricted thereby. Either one of these materials may be employed alone. However, an appropriate mixture thereof can exert improved effects. In the process of the present invention, a wide range of fatty acid derivatives are available, supposedly because each derivative is hydrolyzed in an aqueous medium through a chemical reaction or with the lipase to thereby generate a fatty acid.

The fatty acid or a derivative thereof may be contacted with the water-insoluble carrier by adding these materials to water or an organic solvent as such. However it is preferable that the fatty acid or a derivative thereof is first dispersed or dissolved in the solvent and then added to the insoluble carrier dispersed in water, thus improving its dispersibility. Examples of an appropriate solvent include chloroform and n-hexane. The fatty acid or a derivative thereof and the insoluble carrier may be used in a ratio of 0.01 to 1 part by weight, preferably 0.05 to 0.5 part by weight, of the former, per part by weight, on a dry basis, of the latter, though the present invention is not restricted thereby These materials may be contacted at a temperature of 0° to 100° C., preferably 20° to 60° C. The contact period may range from five minutes to five hours. After the contacting, the carrier may be separated by filtration from the above-mentioned solution and then dried, if required. The drying may be effected at a room temperature to 100° C. It is preferable to effect the drying under reduced pressure to thereby shorten the drying period, though the present invention is not restricted thereby.

In the process of the present invention, the immobilization may be effected at any temperature so long as the enzyme is not inactivated. Namely, it may be effected at 0° to 60° C., preferably 20° to 40° C. The pH value of the enzyme solution may fall within a range where the enzyme is not denatured, i.e., from 3 to 9. When an enzyme having an optimum pH value within the acidic range is to be used, it is preferable to adjust the pH value of the solution to 4 to 6 to thereby achieve the maximum activity. When an enzyme having an optimum pH value within the alkaline range is to be used, on the other hand, it is preferable to adjust the pH value of the solution to 7 to 9. The buffer to be used in the enzyme solution is not particularly specified. Preferable examples thereof include those commonly employed, such as acetate buffer, phosphate buffer and tris hydrochloride buffer.

In the immobilization process of the present invention, the concentration of the enzyme in the aqueous solution thereof is not particularly restricted. From the viewpoint of the immobilization yield, a sufficient concentration thereof below the solubility of the enzyme is desirable. The insoluble matter may be removed by centrifugation and the supernatant may be used, if required. The enzyme and the immobilization carrier may be employed at a ratio of 0.01 to 10 parts by weight, preferably 0.05 to 5 parts by weight, of the former per part by weight of the latter, though the present invention is not restricted thereby.

Examples of esterification with the use of the immobilized enzyme of the present invention include those conducted by using common monohydric alcohols such as methanol, ethanol, propanol or oleyl alcohol, polyhydric alcohols such as propylene glycol, glycerol, sorbitol or polyglycerol, terpene alcohols such as geraniol, citronellol or menthol or sterols such as cholesterol together with saturated or unsaturated fatty acids having 2 to 36, preferably 6 to 24 carbon atoms or lower alcohol esters thereof. Examples of transesterification with the use of the immobilized enzyme of the present invention include acidolysis of esters and fatty acids, alcoholysis among esters and alcohols, transesterification between esters and transphosphatidylation among phospholipids and various alcohols.

The esterification may be carried out at a temperature of 20° to 90° C., preferably 30° to 80° C., without using any solvent or in an inert solvent such as a hydrocarbon or ether. The ratio of the amounts of the alcohol and fatty acid may be adjusted depending on the number of functional groups thereof and the aimed product. When a diglyceride is to be synthesized, for example, approximately two mol of a fatty acid may be employed per mol of glycerol. When a monoglyceride is to be synthesized, on the other hand approximately one mol of a fatty acid may be employed per mol of glycerol.

In the present invention, the carrier may be crosslinked with the use of a polyfunctional reagent prior to immobilization. Thus, the obtained immobilized enzyme has an improved durability when used repeatedly. Examples of the polyfunctional crosslinking agent include polyaldehydes such as glyoxal, glutaraldehyde, malonaldehyde and succinaldehyde. Further, hexamethylene diisocyanate or N,N'-ethylenebismaleimide may be used therefor. Furthermore, carbodimides may be used therefor.

The process of the present invention, which aims at fully utilizing the synthesizing effect of a lipid-decomposing enzyme such as lipase, is based on the finding that an enzyme can be selectively immobilized through adsorption and the esterifying and transesterifying activities of said enzyme can be simultaneously elevated by preliminarily adsorbing a fatty acid or a derivative thereof on an insoluble carrier.

In contrast to the process disclosed in Japanese Patent Laid-Open No. 134090/1987, immobilization is not carried out in the presence of the fatty acid or a derivative thereof, the enzyme and the carrier; The carrier is preliminarily treated with the fatty acid or a derivative thereof in the process of the present invention. This enables selection of a solvent within a wide range. Namely, it is possible in this case that a solid fatty acid such as stearic acid is dissolved in a solvent such as butanol or hexane and then the solvent is removed after the completion of the adsorption. Thus, the carrier may be employed in the subsequent immobilization step.

In a conventional enzymatic esterification process, an equilibrium is established by the water formed with the progress of the reaction, which inhibits further progress of the esterification. Thus, it is attempted to further proceed with esterification by, for example, reducing the pressure within the system. However, it is unavoidable that these treatments lower the esterifying activity of the enzyme. When the immobilized enzyme of the present invention, which sustains a sufficient esterifying activity, even in a system of a low moisture content, is applied to this case, a high esterification ratio can be attained within a short period of time. This is advantageous because the degradation of the product, for example, coloration or the emission of an offensive odor caused by the prolonged reaction can be prevented thereby. In the invention, interesterification and esterification of oil and fats are carried out as mentioned above. Detailed explanation will be made below.

In the process of the present invention, a fatty acid or a derivative thereof is contacted with a water-insoluble carrier in water or an organic solvent to thereby adsorb the former on the latter. The insoluble carrier may be optionally filtered from the solution and dried. Then it is contacted with an aqueous solution of an enzyme or a culture medium containing an enzyme for one minute to 20 hours, preferably for 30 minutes to two hours Then the insoluble carrier is separated by filtration from said solution and washed with water or a buffer. The immobilized enzyme thus obtained is dried. Thus, the immobilized enzyme of the present invention is obtained.

Examples of the enzyme to be used in the present invention include Rhizopus lipases originating from *Rhizopus japonicus, Rhizopus delemar, Rhizopus niveus* and *Rhizopus japanicus*. Those having a site-selectivity and react exclusively at the 1,3-position are particularly preferable.

In the present invention, it is effective for the subsequent continuous transesterification in a column to immobilize the enzyme by contacting the enzyme solution with the insoluble carrier followed by separation of said insoluble carrier by filtration from the solution and drying the same until the moisture content reaches 5% or below, preferably 1.5 to 2%. It is preferable to effect the drying at room temperature to 60° C. under reduced pressure to thereby manifest a high transesterifying activity, though the present invention is not restricted thereby.

The immobilized enzyme of the present invention exerts a high transesterifying activity even at a low moisture content, which makes it possible to attain a sufficiently high reaction rate and to suppress side reactions simultaneously. Thus, the yield and quality of the aimed transesterified fat can be improved.

Examples of the fat to be used in the transesterification process of the present invention include vegetable oils such as soybean oil, olive oil and palm oil as well as animal fats such as beef tallow, lard and fish oil. Although one of these fats may be used alone, it is preferable to employ two or more fats. It is also preferable to transesterify between a fat and a higher fatty acid or between a fat and a lower alcohol ester of a higher fatty acid. When transesterification is effected between a specific fat and another fat, a fatty acid or a derivative thereof, these materials are employed at a ratio of 0.5 to 20 parts by weight, preferably 0.1 to 20 parts by weight, of the other material per part of the specific fat, thus improving the original fat. It is particularly preferable to transesterify a fat comprising a large amount of glycerides having an oleate group at the 2-position, such as a palm oil, with stearic acid. In this reaction, it is required to maintain the temperature of the reaction system at 60° to 90° C. in order to continuously effect the transesterification in a column without using any solvent, since stearic acid has a high melting point while the fat is highly viscous. The immobilized enzyme of the present invention is suitable for this purpose. Further, the resulting fat is useful in the production of chocolate.

The continuous transesterification process by using a column according to the present invention may be carried out in the following manner. A fatty acid or a derivative thereof is contacted with a water-insoluble carrier in water or an organic solvent to thereby adsorb the former on the latter. Then, the carrier is separated by filtration from the solution and dried. Subsequently it is contacted with an aqueous solution a lipase or a culture medium containing a lipase and the carrier is separated by filtration from the solution and washed with water or a buffer. The immobilized lipase thus obtained is dried until the moisture content reaches 1.5 to 2% and packed in a column of an arbitary size. Then the reactant(s) are fed from the top or bottom of the column. A single fat may be used as the reactant. Alternatively two or more fats, a fat and a higher fatty acid, a fat and a lower alcohol ester of a higher fatty acid or a fat and a higher alcohol may be used therefor. When a specific fat is to be transesterified with another fat, a fatty acid or a derivative thereof, these materials should be employed at a rate of 0.05 to 20 parts by weight, preferably 0.1 to 10 parts by weight, of the latter per part by weight of the former in order to achieve a sufficient improvement. In order to achieve the aimed improving effect, it is necessary to adjust the average residence time of the reactant(s) in the column to two hours or shorter, preferably 10 to 60 minutes. When the residence time is excessively long or the employed enzyme has an insufficient activity, the formation of by-products such as saturated triglycerides and diglycerides by side reactions is accelerated and thus the aimed improving effect on the fat can hardly be achieved. Further, it is preferable to adjust the moisture content of a reactant to 0.01 to 0.2% and to control the total moisture content in the reactants in the column to 1.5 to 2.0%, though the present invention is not restricted thereby When the moisture content of the feed materials exceeds 0.2%, the formation of diglycerides caused by hydrolysis (side reaction) is accelerated, which lowers the quality of the aimed product When it is less than 0.01%, on the other hand, no sufficient productivity from the industrial viewpoint can be attained It is preferable to operate the column at a temperature of 40° to 90° C., in particular 60° to 90° C. when a reactant of a melting point higher than 60° C. is used.

The process of the present invention, which aims at fully utilizing the transesterifying activity of a lipase, is based on the finding that an enzyme can be selectively immobilized through adsorption and the transesterifying activity of said enzyme can be simultaneously elevated by preliminarily adsorbing a fatty acid or a derivative thereof on an insoluble carrier.

In contrast to the process disclosed in Japanese Patent Laid-Open No. 134090/1987, the immobilization is not carried out in the presence of the fatty acid or a derivative thereof, the enzyme and the carrier, but the carrier is preliminarily treated with the fatty acid or a derivative thereof in the process of the present invention. This enables selection of a solvent within a wide range. Namely, it is possible in this case that a solid fatty acid such as stearic acid is dissolved in a solvent such as butanol or hexane and then the solvent is removed after the completion of the adsorption. Thus the carrier may be employed in the subsequent immobilization step.

In the process of the present invention, a lipase having a high site-selectivity is immobilized in a highly active state, which enables a high reaction rate to be attained, even in a system of a low moisture content. Therefore, it is possible according to the present invention to suppress the formation of diglyceride by-products, the rearrangement of the asymetric form and the formation of trisaturated glycerides accompanying the same, when a symmetric fat similar to cacao butter in structure is to be prepared through acidolysis between a fat comprising a large amount of glycerides having an oleate group at the 2-position with a saturated fatty acid.

The invention provides another immobilized enzyme which comprises a carrier, a lipid-decomposing enzyme and an oil-soluble compound. It will be explained below. Not only the decomposing activity but also the esterifying and transesterifying activities of an enzyme can be enhanced when said lipid-decomposing enzyme is preset together with one or more oil-soluble compounds selected from among alcohols, ethers, carbonyl compounds and alkyl halides. Based on this finding, the present inventors have further attempted &o adsorb a lipid-decomposing enzyme onto various insoluble carrier together with the abovementioned compound(s), thus completing the present invention.

Accordingly the present invention relates to a lipid-decomposing enzyme immobilized onto an insoluble carrier in the presence of one or more oil-soluble compounds selected from among alcohols, ethers, carbonyl compounds and alkyl halides as well as to esterification and transesterification processes using said lipid-decomposing enzyme.

In the present invention, accordingly, not only selective adsorption and an enhanced decomposing activity f a lipid-decomposing enzyme but also remarkable increases in the esterifying and transesterifying activities thereof are observed when said lipid-decomposing enzyme is preliminarily contacted with an oil-soluble compound(s) in the immobilization of the lipid-decomposing enzyme onto an insoluble carrier by adding said insoluble carrier to a solution containing said enzyme or when said oil-soluble compound(s) are preliminarily adsorbed on said insoluble carrier, optionally dried and then subjected to the immobilization of said enzyme.

The process of the present invention has the following advantages. A first advantage thereof resides in that the aimed enzyme can be highly activated by preliminarily contacting the same with the abovementioned oil-soluble compound(s). As described above, a lipid-decomposing enzyme acting in an interface would show a higher-order structure for the manifestation of its activity when orientated in the interface. In order to achieve this highly active state, a water-soluble material is required. Preferable examples of the water-soluble material include those carrying both hydrophobic and functional groups within a molecule, such as alcohols, ethers, carbonyl compounds and alkyl halide having a relatively large number of carbon atoms. On the other hand, materials forming a nonpolar interface, such as paraffin, can hardly exert such an effect.

A second advantage thereof resides in that the immobilized lipid-decomposing enzyme such as lipase, which would serve, as a matter of course, at the water-fat interface, present on the surface of the carrier can be efficiently utilized. In contrast thereto, when the lipase is used in the form of an aqueous solution, the lipase might be dispersed and equilibrated at the interface and in the aqueous solution, which makes it impossible to fully utilize the enzyme in the solution.

A third advantage thereof resides in that the enzyme can be selectively immobilized at a high yield within a short period of time by adsorbing the abovementioned oil soluble compound(s) on the carrier.

Based on these findings, the present inventors have already completed an invention wherein a lipase is contacted with an insoluble carrier in the presence of a small amount of water and a fat, thus simultaneously orientating the enzyme in the interface and immobilizing the same and applied for a patent (Japanese Patent Laid-Open No. 251884/1985). Subsequently the present inventors have further examined these facts and attempted to apply the same to the preliminary adsorption of oil-soluble compound(s) on various insoluble carriers. As a result, they have succeeded in the preparation of a highly active, immobilized enzyme by contacting an enzyme with the abovementioned carrier, thus simultaneously activating said enzyme and immobilizing the same on said carrier at a high concentration within a short period of time, thus completing the present invention.

Now the present invention will be described in detail.

In the process of the present invention, a lipid-decomposing enzyme is contacted with one or more oil soluble compounds selected from among alcohols, ethers, carbonyl compounds and alkyl halides in an aqueous solution to thereby activate the enzyme Then an insoluble carrier is added to the resulting solution. Alternatively an insoluble carrier, on which said oil-soluble compound(s) have been preliminarily adsorbed, is contacted with an enzyme solution to thereby immobilize the enzyme onto the carrier. Subsequently the insoluble carrier is separated by filtration from the solution and washed with water or a buffer. The immobilized enzyme thus obtained is then dried, if required, to thereby give the immobilized enzyme of the present invention.

The oil-soluble compounds available in the present invention are those which are soluble in one or more of organic solvents such as ethanol, acetone, ether, chloroform or n-hexane but not or hardly soluble in water at room temperature and have 4 to 36, preferably 8 to 24, carbon atoms in total as the hydrophobic moiety.

The oil-soluble alcohols to be used in the present invention is not particularly restricted. Examples thereof include straight-chain and branched aliphatic monohydric alcohols having 4 to 36, preferably 8 to 24, carbon atoms, such as saturated alcohols, for example, octyl alcohol and lauryl alcohol and unsaturated ones, for example, oleyl alcohol and branched ones such as 5-decanol and isostearyl alcohol. Further, dihydric and polyhydric alcohols such as hexamethylene glycol are also available.

In addition, phenol compounds such as alkyl-substituted phenols and sterols such as cholesterol, stigmasterol, brassicasterol and campesterol are also available therefor. Furthermore, terpene alcohols such as phytol, geraniol, farnesol and linalool as well as fat soluble vitamins such as retinol and tocopherol may be employed therefor.

Examples of the ethers include long-chain ethers such as dioctyl ether, glyceryl ethers of thymyl alcohol and batyl alcohol, glyceride-like compounds such as glycidyl ether, polyoxy compounds such as triethylene glycol monomethyl ether and polyethylene glycol monomethyl ether, silicon compounds such as trimethylsylyl ether derivatives of the abovementioned alcohols and polymethylsiloxane.

Examples of the carbonyl compounds include aliphatic aldehydes such as 2,4-decadienal, decanal and hexadecanal, terpene aldehydes such as retinal and aliphatic ketones such as 2-octanone, 2-decanone and octyl decyl ketone.

Examples of the alkyl halides include long-chain alkyl halides such as oleyl chloride, octyl chloride and octyl bromide.

It is preferable from the viewpoint of operation that these oil-soluble compounds are liquid at room temperature, though the present invention is not restricted thereby. Either one of these compounds may be employed alone. However an appropriate mixture thereof can exert improved effects.

The oil-soluble compound(s) may be contacted with the lipid-decomposing enzyme by directly adding the former to an aqueous solution of the latter. However it is preferable that the oil-soluble compound(s) are first dissolved or dispersed and then adding the lipid-decomposing enzyme thereto to thereby improve the dispersion. Examples of a suitable solvent include chloroform, n-hexane and diethyl ether. The oil-soluble compound(s) and the enzyme may be employed at a ratio of 0.001 to 1, preferably 0.01 to 0.5, part by weight of the former per part by weight, on a dry basis, of the latter, though the present invention is not restricted thereby. These materials may be contacted with each other at a temperature of 0° to 100° C. preferably 5° to 60° C. for five minutes to five hours. Subsequently, various insoluble carriers may be added to the enzyme solution thus treated to thereby immobilize the same.

Alternatively, the process of the present invention may be carried out by preliminarily adsorbing the abovementioned oil-soluble compound(s) on various insoluble carriers. The adsorption may be effected by dispersing an insoluble carrier in an aqueous solution and then directly adding the oil-soluble compound(s) thereto. However it is preferable to first dissolve or disperse the carrier in a solvent in order to effect an improved dispersion. Examples of an appropriate solvent include chloroform, n-hexane and diethyl ether. These oil-soluble compound(s) and the insoluble carrier may be used at a ratio of 0.001 to 1, preferably 0.01 to 0.5, part by weight of the former per part by weight, on a dry basis, of the latter, though the present invention is not restricted thereby. After the contacting, the carrier may be separated by filtration from the above solution and dried, if required. Then the insoluble carrier thus treated is contacted with an aqueous solution of the enzyme or a fermentation liquor containing the same to thereby effect the immobilization.

In the present invention, the contact period of the enzyme and the carrier may range from five minutes to 20 hours, preferably from 30 minutes to two hours. After the contacting, the carrier may be separated by filtration from the solution and dried, if required. The drying may be effected at room temperature to 80° C. It is preferable to effect the drying under reduced pressure to thereby shorten the drying period, though the present invention is not restricted thereby.

In the present invention, the immobilization may be effected at any temperature so long as the enzyme is not inactivated. Namely, it may be effected at 0° to 60° C., preferably 20° to 40° C. The pH value of the enzyme solution may fall within a range where the enzyme is not denatured, i.e., from 3 to 9. When an enzyme having an optimum pH value within the acidic range is to be used, it is preferable to adjust the pH value of the solution to 4 to 6 to thereby achieve the maximum activity. The buffer to be used in the enzyme solution is not particularly specified. Preferable examples thereof include those commonly employed, such as acetate buffer, phosphate buffer and tris hydrochloride buffer.

In the immobilization process of the present invention, the concentration of the enzyme in the aqueous solution thereof is not particularly restricted. From the viewpoint of immobilization yield, a sufficient concentration thereof below the solubility of the enzyme is desirable. The insoluble matter may be removed by centrifugation and the supernatant may be used, if required. The enzyme and the immobilization carrier may be employed at a ratio of 0.01 to 10 parts by weight, preferably 0.05 to 5 parts by weight, of the former per part by weight of the latter, though the present invention is not restricted thereby.

In the present invention, the carrier may be crosslinked by the use of a polyfunctional reagent prior to the immobilization. Thus, the obtained immobilized enzyme has an improved durability when used repeatedly. Examples of the polyfunctional crosslinking agent include polyaldehydes such as glyoxal, glutaraldehyde, malonaldehyde and succinaldehyde. Further, hexamethylene diisocyanate or N,N'-ethylenebismaleimide may be used therefor. Furthermore, carbodimides may be used therefor.

In the invention, the immobilized enzyme is preferably prepared by mixing a water-insoluble, volatile, organic solvent with an insoluble carrier, adding a lipid-decomposing enzyme, dissolved or dispersed in an aqueous medium, thereto, separating said insoluble carrier and drying the same until the moisture content thereof reaches 5% by weight or below.

In the present invention, not only the decomposing activity of a lipid-decomposing enzyme but also the esterifying and transesterifying activities thereof can be enhanced by preliminarily adsorbing oil-soluble compound(s) such as fatty acids, derivatives thereof, alcohols, ethers, carbonyl ecompounds and alkyl halides on the insoluble carrier. Based on this finding, the present inventors have further attempted to adsorb said oil-soluble compound(s) an various insoluble carriers together with a lipid-decomposing enzyme in a water-insoluble volatile organic solvent.

In the process of the present invention, which comprises mixing a water-insoluble volatile organic solvent with an insoluble carrier and adding a lipid-decomposing enzyme dissolved or dispersed in an aqueous medium to the resulting mixture, one or more oil-soluble compounds, selected from among fatty acids, derivatives thereof, alcohols, ethers, carbonyl compounds and alkyl halides, are adsorbed on the insoluble carrier in the water-insoluble, volatile, organic solvent by contact therewith prior to the addition of the enzyme solution. Then the enzyme solution is added to the obtained dispersion to thereby adsorb and immobilize the lipid-decomposing enzyme onto the carrier. Subsequently, the insoluble carrier is separated by filtration from the solution and washed with deionized water or a buffer. The immobilized enzyme thus obtained is dried until the moisture content thereof reaches 5% by weight or below. Thus, the immobilized enzyme of the present invention is obtained.

Examples of the water-insoluble volatile organic solvent to be used in the present invention include organic chlorinated solvents such as chloroform and carbon tetrachloride, hydrocarbon solvents such as n-hexane and petroleum ether, ethers such as diethyl ether and dimethyl ether and lower alcohols such as butanol, pentanol, hexanol and heptanol. The water-insoluble volatile organic solvent may be preferably used at a ratio of 1 to 100 parts by weight per part by weight of the insoluble carrier and 0.1 to 10 parts by weight, preferably 0.3 to 3 parts by weight, per part by weight of water, though the present invention is not restricted thereby.

The oil-soluble compound(s) may be contacted with the lipid-decomposing enzyme in the following manner. The oil-soluble compound(s) are dispersed or dissolved in a water-insoluble, volatile, organic solvent and an insoluble carrier is added thereto. Thus, the oil-soluble compound(s) are preliminarily adsorbed on the carrier. Then the enzyme is added to the solution to thereby immobilize the same. The enzyme is preliminarily dispersed or dissolved in an aqueous medium such as water or a buffer. Alternatively, a filtrate obtained by filtering off cells from a fermentation liquor may be directly employed therefor.

The oil-soluble compound(s) and the insoluble carrier are used preferably at a ratio of 0.001 to 1 part by weight of the former to part by weight of the latter, though the present invention is not restricted thereby. It is undesirable to use an excessively large amount of the oil-soluble compound(s), because they are not adsorbed on the insoluble carrier but liberated into the solution to adsorb the enzyme, thus lowering the yield of immobilization. The adsorption may be preferably carried out at 0° to 60° C., more preferably 5° to 30° C., for five minutes to two hours, though the present invention is not restricted thereby.

It is appropriate to immobilize 0.001 to 1 part by weight, on a dry basis, of the enzyme per part by weight of the insoluble carrier, though the present invention is not restricted thereby.

It is preferable that the immobilization is effected at 0° to 40° C., more preferably 5° to 30° C., though the present invention is not restricted thereby. An appropriate contacting period ranges from five minutes to five hours.

The immobilized enzyme thus obtained is dried until the moisture content reaches 5% by weight or below. When the immobilized enzyme of the present invention is to be used in a continuous operation by using a column, it is preferable to dry the same until the moisture content reaches 1 to 2% by weight. It is preferable that the drying is effected at room temperature to 80° C. and under reduced pressure, in order to facilitate the drying, though the present invention is not restricted thereby. The drying rate is not particularly critical in the manifestation of the enzyme activity. However, a drying rate as high as possible is preferable from the viewpoint of operation.

The enzyme is dispersed or dissolved in an aqueous medium such as a buffer prior to the use. Insoluble matters may be removed by, for example, centrifugation or filtration, if required.

The pH value of the enzyme solution may fall within a range where the enzyme is not denatured, i.e., from 3 to 9. The buffer to be used in the enzyme solution is not particularly specified. Preferable examples thereof include those commonly employed, such as acetate buffer, phosphate buffer and tris hydrochloride buffer.

As described above, the present invention, wherein the esterifying and transesterifying activities of a lipid-decomposing enzyme can be enhanced by immobilizing said enzyme in an activated state, enables an immobilized enzyme to be readily and economically prepared on an industrial scale.

EXAMPLES

To further illustrate the present invention, the following Examples and Comparative Examples will be given.

EXAMPLE 1

10 g of a commercially available weak anion exchange resin (phenol/formaldehyde resin: Duolite A-568 mfd. by Diamond Shamrock Chemical Co.) was added to 100 ml of deionized water. Then, 2 g of oleic acid (lunac O-LL, tradename, produced by Kao Corporation, formerly named Kao Soap Co., Ltd.) was added thereto and the obtained mixture was stirred at 30° C. for 30 minutes. Then, the resin was separated by filtration from the solution and washed with deionized water.

10 g of a commercially available lipase preparation originating from *Rhizopus japonicus* (19,000 U/g: Lipase A10 mfd. by Osaka Saikin Kenkyusho, K. K.) was dissolved in 100 ml of a 10 mM acetate buffer (pH 4.5). To the resulting solution was added the resin prepared above and the solution was stirred for two hours. Subsequently, the resin was separated by filtration from the suspension and washed with water. The activity yield determined from the lipase activity of the filtrate in this stage was 96%, which suggested that most of the added lipase was adsorbed and immobilized. Then, it was dried at room temperature under reduced pressure until the moisture content reached 5% to thereby give an immobilized lipase.

1 g of the immobilized lipase thus obtained was mixed with 23 g of glycerol (moisture content 0.8%, mfd. by Kao Soap Co., Ltd.) and 70.5 g of oleic acid and the mixture was esterified at 40° C. while stirring. The acid value of the reaction mixture was monitored by sampling part of the same with the lapse of time and analyzing each sample according to the standard analytical method for fats. Thus, the esterification ratio was calculated according to the following equation:

$$\text{esterification ratio} (\%) = 1 - \left(\frac{AV_t}{AV_0}\right) \times 100$$

wherein $AV_t$ represents the acid value of a sample taken after t hours; and $AV_0$ represents that of the mixture determined before the reaction.

COMPARATIVE EXAMPLE 1

The procedure of Example 1 was repeated except that the commercially available resin was not treated with oleic acid and was directly subjected to the immobilization of the lipase. The adsorption ratio and esterification ratio were calculated in the same manner. Table 1 shows the results.

TABLE 1

| | Adsorption ratio of enzyme (%) | Esterification ratio after 3 hr (%) |
|---|---|---|
| Ex. 1 | 96.0 | 87.0 |
| Comp. Ex. 1 | 66.2 | 11.0 |

EXAMPLE 2

The procedure of Example 1 was repeated except that the oleic acid was substituted by oleic triglyceride (reagent: mfd. by Tokyo Kasei K. K.), oleic diglyceride (reagent: mfd. by Tokyo Kasei K. K.), oleic monoglyceride (reagent: Excel 0-95 mfd. by Kao Soap Co., Ltd.) and ethyl oleate (reagent: mfd. by Tokyo Kasei K. K.), each as a fatty acid ester.

1-g portions of the immobilized lipases obtained in this Example, Example 1 and Comparative Example were reacted each with 10 g of a medium-melting fraction of palm oil (iodine value: 32.5, diglyceride content: 4.6%) and 10 g of commercially available stearic acid (Lunac S-90 mfd. by Kao Soap Co., Ltd.; stearic acid purity: 93%) at 70° C. for two hours. After the completion of the reaction, glyceride fractions were separated by column chromatography (stationary phase: Florisil mfd. by Floridin Co.; solvent: hexane/ethyl ether (2:3)). The amount of stearic acid contained in the glyceride was determined by gas chromatography and the reaction ratio was calculated according to the following equation with the equilibrium value being 100%:

$$\text{reaction ratio after } t \text{ hr} (\%) = 100 \times \frac{S_t - S_0}{S_\infty - S_0}$$

wherein $S_t$ represents the stearic acid content of the fat after t hr;

$S_0$ represents that of the material fat; and $S_\infty$ represents that in the 1,3-random equilibrium.

Table 2 summarizes the results. It suggests that an equilibrium was achieved in each case of the present invention within five hours accompanied by the formation of less by-products than in the case of the Comparative Example.

TABLE 2

| Fatty acid derivative | After 2 hr | |
|---|---|---|
| | Reaction ratio (%) | Diglyceride (%) |
| Oleic acid (Ex. 1) | 64.2 | 10.5 |
| Oleic triglyceride | 61.7 | 10.4 |
| Oleic diglyceride | 68.5 | 10.2 |
| Oleic monoglyceride | 67.5 | 11.0 |
| Ethyl oleate | 68.6 | 10.9 |
| Comp. Ex. | 5.6 | 5.9 |

EXAMPLE 3

The procedure of Example 1 was repeated except that the oleic acid in the pretreatment of the carrier was substituted with linoleic acid, lauric acid, stearic acid and ricinoleic acid (each a reagent mfd. by Tokyo Kasei K. K.) and isostearic acid (Diadol mfd. by Mitsubishi Chemical Industries, Ltd.). Each immobilized enzyme thus obtained was used in the transesterification in the same manner as the one described in Example 2.

Table 3 summarizes the results.

TABLE 3

| Fatty acid | After 2 hr | |
|---|---|---|
| | Reaction ratio (%) | Diglyceride (%) |
| Linoleic acid | 98.5 | 11.1 |
| Lauric acid | 85.6 | 11.8 |
| Stearic acid | 90.5 | 10.8 |
| Ricinoleic acid | 92.9 | 9.8 |
| Isostearic acid | 91.7 | 10.2 |

EXAMPLE 4

The procedure of Example 1 was repeated except that oleic acid used in the pretreatment of the resin was substituted with propylene glycol monoleate (Sun-Soft 25-0 mfd. by Taiyo Kagaku K. K.), sorbitan monooleate (Emusol 0-10 mfd. by Kao Soap Co., Ltd.), triglycerol pentaoleate (PO-310 mfd. by Sakamoto Yakuhin K. K.) and sucrose monooleate (Ryoto Ester 0-1570 mfd. by Mitsubishi Kasei Shokuhin K. K.), each employed as a fatty acid polyhydric alcohol ester. Each immobilized enzyme thus obtained was employed in transesterification in the same manner as the one described in Example 2.

Table 4 summarizes the results.

TABLE 4

| Fatty acid derivative | After 2 hr | |
|---|---|---|
| | Reaction ratio (%) | Diglyceride (%) |
| Propylene glycol monooleate | 91.5 | 10.3 |
| Sorbitan monooleate | 91.4 | 11.3 |
| Triglycerol pentaoleate | 86.2 | 11.4 |
| Sucrose monooleate | 78.0 | 8.8 |

EXAMPLE 5

In this Example, organic carriers were examined

The procedure of Example 1 was repeated except that the weak anion exchange resin was substituted with Duolite A-7, Duolite ES-562, Duolite ES-771 and Duolite A-368, each mfd. by Diamond Shamrock Chemical Co. and used as a macroporous weak anion exchange resin; Duolite S-762 (mfd. by Diamond Shamrock Chemical Co.) as a phenol adsorptive resin; Diaion WA30 (mfd. by Mitsubishi Chemical Industries Ltd.) as a macroporous anion exchange resin; and chitosan (Chitopearl BC-300 mfd. by Fuji Spinning Co. Ltd.).

Each immobilized lipase thus obtained was used in transesterification in the same manner as the one described in Example 2. Table 5 summarizes the results.

TABLE 5

| Resin | After 2 hr | |
|---|---|---|
| | Reaction ratio (%) | Diglyceride (%) |
| Duolite A-7 | 68.0 | 7.8 |
| Duolite ES-562 | 87.9 | 9.8 |
| Duolite ES-771 | 80.0 | 9.0 |
| Duolite A-368 | 57.3 | 7.2 |
| Duolite S-762 | 82.1 | 9.2 |
| Diaion WA30 | 77.8 | 7.8 |
| Chitopearl BC-3000 | 56.4 | 8.7 |

EXAMPLE 6

In this Example, inorganic carriers were examined

The procedure of Example 1 was repeated except that the weak anion exchange resin was substituted with calcium silicate (Flowlite R mfd. by Tokuyama Soda Co., Ltd.), synthetic zeolite (Mizuka Sieves 5A mfd. by Mizusawa Industrial Chemicals Ltd.), silica beads (Silbead N mfd. by Mizusawa Industrial Chemicals Ltd.) and spherical alumina (Neobead D mfd. by Mizusawa Industrial Chemicals Ltd.).

Each enzyme thus obtained was used in transesterification in the same manner as described in Example 2. Table 6 shows the results.

TABLE 6

| Inorganic carrier | After 2 hr | |
|---|---|---|
| | Reaction ratio (%) | Diglyceride (%) |
| Flowlite R | 60.0 | 9.3 |
| Silbead N | 52.0 | 8.9 |
| Neobead D | 55.3 | 7.7 |
| Mizuka Sieves | 61.3 | 9.8 |

These results indicate that the effects of the present invention can be achieved by using porous adsorptive resins, natural polymers and porous inorganic carriers in addition to ion exchange resins.

EXAMPLE 7

The immobilizing process of Example 1 was repeated except that a commercially available lipase originating from *Rhizopus delemar* (Talipase mfd. by Tanabe Seiyaku Co., Ltd.) was employed.

EXAMPLE 8

The immobilizing process of Example 1 was repeated except that a commercially available lipase originating from *Mucor sp.* (Lipase M mfd. by Amano Seiyaku K. K.) was employed.

EXAMPLE 9

The immobilizing process of Example 1 was repeated except that a commercially available lipase originating from *Penicillium cyclopium* (Lipase G mfd. by Amano Seiyaku K. K.) was employed.

COMPARATIVE EXAMPLE 2

The procedure of Example 7 was repeated except that the carrier was not treated with oleic acid and was directly subjected to the immobilization of lipase.

COMPARATIVE EXAMPLE 3

The procedure of Example 8 was repeated except that the carrier was not treated with oleic acid and was directly subjected to the immobilization of lipase.

COMPARATIVE EXAMPLE 4

The procedure of Example 9 was repeated except that the carrier was not treated with oleic acid and was directly subjected to the immobilization of lipase.

Each immobilized lipase obtained in the above Examples 7 to 9 and Comparative Example 2 to 4 was used in esterification in the same manner as the described in Example 1. Table 7 summarizes the results. These results indicate that other lipases would show activities comparable to that of the lipase employed in Example 1.

TABLE 7

| Enzyme source | Adsorption ratio of enzyme (%) | Esterification ratio after 3 hr (%) |
| --- | --- | --- |
| Ex. 7 | 96.1 | 99.4 |
| Comp. Ex. 2 | 20.1 | 57.3 |
| Ex. 8 | 88.3 | 50.6 |
| Comp. Ex. 3 | 72.0 | 35.5 |
| Ex. 9 | 90.4 | 90.3 |
| Comp. Ex. 4 | 52.0 | 32.1 |

EXAMPLE 10

The immobilizing process of Example 2 was repeated except that the fatty acid derivative was substituted with commercially available soybean lecithin (reagent mfd. by Wako Pure Chemicals Ltd.), phosphatidylcholine, phosphatidylserine, phosphatidylinositol, phosphatidylethanolamine and phosphatidic acid, each used alone. 10 ml portions of butanol were used in order to facilitate the dispersion of each of the phospholipids.

Each immobilized enzyme thus obtained was used in esterification in the same manner as described in Example 2. Table 8 summarizes the results.

Table 8 obviously indicates that these phospholipids would also bring about significant effects.

TABLE 8

| Phospholipid | After 2 hr Reaction ratio (%) | After 2 hr Diglyceride (%) |
| --- | --- | --- |
| Soybean lecithin | 97.3 | 10.2 |
| Phosphatidylcholine | 54.3 | 8.6 |
| Phosphatidylserine | 59.8 | 9.5 |
| Phosphatidylinositol | 88.6 | 9.8 |
| Phosphatidylethanolamine | 55.8 | 9.3 |
| Phosphatidic acid | 80.6 | 9.7 |

TEST EXAMPLE 1

50 g of the immobilized enzyme obtained in Example 1 was packed in a column (125 ml) provided with a jacket. The mixture (1:1) of a medium-melting fraction of palm oil and stearic acid used in Example 2 was continuously passed through the column at a column temperature of 70° C. and at a flow rate of 180 g/hr and the reaction ratio at the outlet of the column was examined As a result, the reaction ratio at the outlet was maintained at 85% after 1,400 hours. During this period, approximately 5,000 kg of the fat was treated per kg of the immobilized enzyme.

This result proves that the immobilized enzyme obtained by the process of the present invention has an extremely high durability.

EXAMPLE 11

50 g of the immobilized enzyme obtained in Example 1 was dried until the moisture content reached 1.8% and packed in a column (125 ml) provided with a jacket. The mixture (1:1, moisture content 0.10%) of a medium-melting fraction of palm oil and stearic acid used in Example 1 was continuously passed through the column at a column temperature of 70° C. at a flow rate of 180 g/hr and the reaction ratio at the outlet of the column was examined The average residence time in the column was approximately 40 minutes. The moisture content, based on the reactant, was 1.75% and the initial reaction ratio was 98%. The reaction ratio at the outlet was maintained at 85% after 1,400 hours During this period, approximately 5,000 kg of the fat was treated per kg of the immobilized enzyme.

EXAMPLE 12

The immobilized enzyme obtained in Example 3 was dried until the moisture content reached 1.8% and 50 g of the same was packed in the same column (125 ml) provided with a jacket as used in Example 8. A mixture (moisture content: 0.15%) of one part by weight of a medium melting fraction of palm oil and two parts by weight of stearic acid used in Example 1, molten by heating to 70° C., was continuously fed from the top of the column at a flow rate of 160 g/hr and the reaction ratio at the outlet of the column was examined. The average residence time in the column was approximately 47 minutes. The moisture content, based on the reactant, was 1.81% and the initial reaction ratio was 95%. The reaction ratio at the outlet was maintained at 80% after 1,250 hours. During this period, approximately 4,000 kg of the fat was treated per kg of the immobilized enzyme.

These results prove that the immobilized enzyme treated according to the present invention is highly active and highly durable on a practical level.

EXAMPLE 13

The procedure of Example 1 was repeated except that the oleic acid used in pretreatment was substituted with ricinoleic acid and that 10-g portions of commercially available lipases originating from Rhizopus spp., namely, R. delemar (Lipase D mfd. by Amano Seiyaku K. K., 8348 U/g), R. niveus (Lipase N mfd. by Amano Seiyaku K. K., 31250 U/g), and R. javanicus (Lipase F mfd. by Amano Seiyaku K. K., 97500 U/g) were used.

Then, each immobilized lipase thus obtained was used in transesterification similar to Example 1.

COMPARATIVE EXAMPLE 5

The procedure of Example 13 was repeated except that the commercially available resin was not treated with ricinoleic acid but was directly subjected to the immobilization of the lipase.

The immobilized lipase thus obtained was used in transesterification similar to Example 1.

Table 9 summarizes the results of Example 13 and Comparative Example 5.

TABLE 9

| Lipase | Pretreatment | After 2 hr | |
|---|---|---|---|
| | | Reaction ratio (%) | Diglyceride (%) |
| Lipase D | yes | 83.8 | 13.7 |
| | no | 12.7 | 7.6 |
| Lipase N | yes | 33.1 | 11.7 |
| | no | 9.8 | 6.0 |
| Lipase F | yes | 71.4 | 12.0 |
| | no | 11.6 | 7.5 |

These results indicate that the process of the present invention is effective with *Rhizopus lipases* in general

EXAMPLE 14

10 g of a commercially available lipase originating from *Rhizopus japonicus* (Lipase A10 mfd. by Osaka Saikin Kenkyusho, K. K.: 35,000 U/g) was dissolved in 100 ml of a 10 mM acetate buffer (pH 5.0).

To 150 ml of n-hexane, 10 g of a weak anion exchange resin (phenol/formaldehyde resin: Duolite A-568 mfd. by Diamond Shamrock Chemical Co.) was added and stirred for 30 minutes. 100 ml of the aqueous solution of the enzyme obtained above was added by portions to the carrier dispersion and stirred for two hours. Then, the resin was separated by filtration from the suspension, washed with water and dried at room temperature and under a reduced pressure until the moisture content thereof reached 5% or below. Thus, an immobilized lipase was obtained.

1-g portions of the immobilized lipase (moisture content 4.6%) thus obtained were each reacted with 10 g of a medium-melting fraction of palm oil (iodine value: 32.5, diglyceride content 4.6%) and 10 g of commercially available stearic acid (Lunac S-90 mfd. by Kao Soap Co., Ltd.; stearic acid purity: 93%) at 70° C. for two hours. Results are shown in Table 10 in terms of a reaction ratio after t hour.

COMPARATIVE EXAMPLE 6

10 g of the commercially available lipase used in Example 14 was dissolved in 100 ml of a 10 mM acetate buffer (pH 5.0).

To the resulting solution, 10 g of a commercially available weak anion exchange resin (Duolite A-568) used in Example 14 was added and stirred for two hours. Then, the carrier resin was separated by filtration from the suspension, washed with deionized water and dried at room temperature under reduced pressure until the moisture content reached 5% or below. Thus, an immobilized lipase was obtained.

The immobilized lipase thus obtained was used in esterification in the same manner as described in Example 14. Table 10 shows results.

EXAMPLE 15

10 g of the commercially available lipase used in Example 14 was dissolved in 100 ml of a 10 mM acetate buffer (pH 5.0).

10 g of a commercially available weak anion exchange resin (Duolite A-568) used in Example 14 was added to 150 ml of n-hexane and 2 g of ricinoleic acid (Rishinolein-San mfd. by Ito Seiyu K. K.) was added to the dispersion and stirred for 30 minutes. 100 ml of the enzyme solution prepared above was added, by portions, to the carrier dispersion and stirred for two hours. Then, the carrier resin was separated by filtration from the suspension, washed with deionized water and dried at room temperature and under a reduced pressure until the moisture content reached 5% or below. Thus, an immobilized lipase was obtained.

The immobilized lipase thus obtained was used in transesterification in the same manner as described in example 14. Table 10 shows results.

TABLE 10

| | After 5 hr | |
|---|---|---|
| | Reaction ratio (%) | Diglyceride (%) |
| Ex. 14 | 57.3 | 8.8 |
| Ex. 15 | 81.5 | 8.6 |
| Comp. Ex. 6 | 5.6 | 5.9 |

Table 10 obviously indicates that the reaction sufficiently proceeded within five hours when each immobilized enzyme of the present invention was used.

EXAMPLE 16

10 g of a commercially available lipase originating from *Rhizopus japonicus* (Lipase A10 mfd. by Osaka Saikin Kenkyusho K. K.: 35,000 U/g) was dissolved in 100 ml of a 10 mM acetate buffer (pH 5.0).

To the resulting solution, 2 g of octyl alcohol (reagent: Tokyo Kasei K. K.) was added and contacted therewith at 20° C. for 30 minutes.

According to a method reported by Fukumoto et al. (cf. J. Gen. Appl. Microbiol., 98, 353 (1963)), a specified amount of the lipase solution was added to 5 ml of an olive oil emulsion and 4 ml of a 0.1M phosphate buffer and reacted at 37° C. for 30 minutes. The amount of the fatty acid thus formed, which corresponded to 1 $\mu$mol min in terms of oleic acid, was referred to as 1 U. Thus the lipase activity was determined. As a result, the lipase activity was elevated 1.5-fold, compared with a control case wherein no octyl alcohol was added.

To 100 ml of the mixture of octyl alcohol with lipase, 10 g of a weak anion exchange resin (phenol/formaldehyde resin: Duolite A-568 mfd. by Diamond Shamrock Chemical Co.) was added and stirred for 30 minutes. Thus, the lipase to which the oleyl alcohol was bound was adsorbed on the carrier. Subsequently, the resin was separated by filtration from the solution and washed with deionized water. The lipase activity of the filtrate indicated that 92% of the added lipase was immobilized. The resin thus obtained was dried at room temperature under reduced pressure until the moisture content reached 5%. Thus, the aimed immobilized enzyme was obtained.

EXAMPLE 17

10 g of a commercially available weak anion exchange resin (phenol/formaldehyde resin: Duolite A-568 mfd. by Diamond Shamrock Chemical Co.) was added to 100 ml of deionized water. Then 2 g of octyl alcohol (reagent mfd. by Tokyo Kasei K. K.) was added thereto and the obtained mixture was stirred at 30° C. for 30 minutes. Then, the resin was separated by filtration from the solution and washed with deionized water.

10 g of a commercially available lipase preparation used in Example 1 was dissolved in 100 ml of a 10 mM acetate buffer (pH 5.0). To the resulting solution was added the resin prepared above and it was stirred for two hours. Subsequently, the resin was separated by filtration from the suspension and washed with water. The activity yield determined from the lipase activity of the filtrate in this stage was 96%, which suggested that most of the added lipase was adsorbed and immobilized.

Then, it was dried at room temperature and under a reduced pressure until the moisture content reached 5% to thereby give an immobilized lipase.

COMPARATIVE EXAMPLE 7

The procedure of Example 17 was repeated except that the commercially available resin used in Example 17 was directly employed to thereby give an immobilized lipase.

EXAMPLE 18

The procedure of Example 17 was repeated except that octyl alcohol was substituted with oleyl alcohol to thereby give an immobilized lipase.

EXAMPLE 19

1-g portions of the immobilized lipases obtained in examples 16 &o 18 and Comparative Example 7 were each mixed with 9.8 g of oleyl alcohol (reagent mfd. by Tokyo Kasei K. K.) and 10.2 g of oleic acid (reagent mfd. by Tokyo Kasei) The resulting mixture was esterified while stirring at 65° C. Ten minutes after the initiation of the reaction, a portion of the reaction mixture was sampled and the acid value thereof was determined according to the standard method for analyzing fats. Thus, the esterification rate was calculated according to the following equation:

$$\text{esterification rate } (\mu\text{mol/min} \cdot g) = \frac{AV \times SW \times 1000}{56.1 \times 10 \times EW}$$

wherein AV represents the acid value of the sample after 10 minutes;
SW represents the weight (g) of the sample; and
EW represents the weight (g) of the enzyme.
Table 11 shows the results.

TABLE 11

| Immobilized lipase | Adsorption of enzyme (%) | Esterification rate (μmol/min · g) |
|---|---|---|
| Ex. 16 | 74.2 | 390.8 |
| Ex. 17 | 96.5 | 450.0 |
| Ex. 18 | 95.2 | 1406.8 |
| Comp. Ex. 7 | 66.2 | 129.8 |

EXAMPLE 20

The procedure of Example 17 was repeated except that the octyl alcohol was substituted with oleyl chloride (reagent mfd. by Tokyo Kasei K. K.) to thereby give an immobilized enzyme.

EXAMPLE 21

1-g portions of the immobilized lipases obtained in examples 16 to 18 and 20 and Comparative Example 7 were each reacted with 10 g of a medium-melting fraction of palm oil (iodine value: 32.5, diglyceride content: 4.6%) and 10 g of commercially available stearic acid (Lunac S-90 mfd. by Kao Soap Co., Ltd.; stearic acid purity: 93%) at 70° C. for two hours.

Table 12 summarizes the results. It suggests that an equilibrium was achieved in each case of the present invention within five hours accompanied by the formation of less by-products than in the case of Comparative Example 7.

TABLE 12

| | After 5 h | |
|---|---|---|
| Immobilized lipase | Reaction ratio (%) | Diglyceride (%) |
| Ex. 16 | 75.7 | 9.8 |
| Ex. 17 | 96.8 | 10.9 |
| Ex. 18 | 95.7 | 13.8 |
| Ex. 20 | 81.0 | 9.5 |
| Comp. Ex. 7 | 5.6 | 5.9 |

EXAMPLE 22

10 g of the commercially available lipase used in Example 16 was dissolved in 100 ml of a 50 mM acetate buffer (pH 5). To the resulting solution were added 2-portions of farnesol (reagent mfd. by Wako Pure Chemical Inc.), geraniol (mfd. by Takasago Perfumery Co., Ltd.) and phytol (reagent mfd. by Tokyo Kasei) and it was stirred at 20° C. for 30 minutes. Then 10 g of the commercially available weak anion exchange resin used in Example 16 was added to the above enzyme/oil-soluble compound mixture and stirred for two hours. The resin was separated by filtration from the solution and washed with deionized water. Then, it was dried at room temperature and under a reduced pressure until the moisture content reached 5%. Thus, immobilized lipases were obtained.

Table 13, which shows the adsorption ratios of the enzyme, indicates that the enzyme was immobilized at a high yield in each case.

The immobilized enzymes thus obtained were employed in esterification and transesterification in the same manner as those described in Examples 19 and 21. As a result, each enzyme showed a high activity.

Tables 14 and 15 show the results.

TABLE 13

| Oil-soluble compound | Enzyme adsorption ratio (%) |
|---|---|
| Farnesol | 91.8 |
| Geraniol | 97.9 |
| Phytol | 92.2 |

TABLE 14

| Oil-soluble compound | Esterification rate (μmol/min · g) |
|---|---|
| Farnesol | 976.8 |
| Geraniol | 996.6 |
| Phytol | 1034.0 |

TABLE 15

| | Transesterification after 5 hr | |
|---|---|---|
| Oil-soluble compound | Reaction ratio (%) | Diglyceride (%) |
| Farnesol | 91.1 | 11.5 |
| Geraniol | 93.4 | 11.4 |
| Phytol | 90.0 | 10.6 |

EXAMPLE 23

The procedure of Example 17 was repeated except that the octyl alcohol was substituted with trimethylsilyl (TMS) ether of oleyl alcohol to thereby give an immobilized lipase.

The immobilized lipase thus obtained was used in transesterification in the same manner as the one described in Example 21. Table 16 shows the results.

TABLE 16

| Oil-soluble compound | Transesterification after 5 hr | |
|---|---|---|
| | Reaction ratio (%) | Diglyceride (%) |
| TMS ether of oleyl alcohol | 97.3 | 8.7 |

We claim:

1. An immobilized enzyme-carrier combination comprising an insoluble carrier made of a phenol/formaldehyde resin, a fatty acid or derivative thereof selected from the group consisting of linoleic acid, lauric acid, stearic acid, ricinoleic acid and isostearic acid and a lipolytic enzyme derived from *Rhizopus japonicus*, said immobilized enzyme-carrier combination being prepared by providing the insoluble carrier, adsorbing the fatty acid or derivative thereof onto the insoluble carrier by contacting said carrier therewith and adsorbing and immobilizing the lipolytic enzyme onto said insoluble carrier containing said adsorbed fatty acid or derivative thereof by contacting said lipolytic enzyme therewith.

2. An immobilized enzyme carrier combination as claimed in claim 1 in which the carrier is macroporous.

3. An immobilized enzyme-carrier combination as claimed in claim 1, in which the immobilization of the enzyme is conducted by mixing a water-insoluble volatile organic solvent with the carrier, adsorbing the fatty acid or derivative thereof on the carrier, separately dispersing or dissolving the enzyme in an aqueous medium, adding the enzyme to the mixture of the solvent and the carrier, separating the carrier from the mixture and drying the carrier having the immobilized enzyme thereon until its water content reaches 5 wt. % or below.

4. An immobilized enzyme-carrier combination as claimed in claim 1, in which the lipolytic enzyme is adsorbed and immobilized on the insoluble carrier containing said fatty acid or derivative thereof in an aqueous medium.

5. An immobilized enzyme-carrier combination as claimed in claim 1, in which said fatty acid or derivative thereof is ricinoleic acid.

6. In a process for producing an ester from a lower mono- or polyhydric alcohol and a higher fatty acid in the presence of an immobilized enzyme-carrier combination, the improvement comprising utilizing an immobilized enzyme-carrier combination prepared by providing an insoluble carrier made of a phenol/formaldehyde resin, adsorbing a fatty acid or derivative thereof selected from the group consisting of linoleic acid, aluric acid, stearic acid, recinoleic acid and isostearic acid onto the insoluble carrier by contacting said carrier therewith and adsorbing and immobilizing a lipolytic enzyme derived from *Rhizopus japonicus* onto said insoluble carrier containing said adsorbed fatty acid or derivative thereof by contacting said lipolytic enzyme therewith.

7. A process as claimed in claim 6, in which the lipolytic enzyme is adsorbed and immobilized on the insoluble carrier containing said fatty acid or derivative thereof in an aqueous medium.

8. A process as claimed in claim 6, in which said fatty acid or derivative thereof is ricinoleic acid.

9. In a process for interesterification of fats and oils in the presence of an immobilized enzyme-carrier combination, the improvement comprising utilizing an immobilized enzyme-carrier combination prepared by providing an insoluble carrier made of a phenol/formaldehyde resin, adsorbing a fatty acid or derivative thereof selected from the group consisting of linoleic acid, lauric acid, stearic acid, ricinoleic acid and isostearic acid onto the insoluble carrier by contacting said carrier therewith and adsorbing and immobilizing a lipolytic enzyme derived from *Rhizopus japonicus* onto said insoluble carrier containing said adsorbed fatty acid or derivative thereof by contacting said lipolytic enzyme therewith.

10. A process as claimed in claim 9, in which the immobilized enzyme carrier combination is dried so as to have a water content of 2 wt. % or below, a reaction column is charged with the resulting immobilized enzyme carrier combination and interesterification is continuously carried out without the use of a solvent.

11. A process as claimed in claim 10, in which starting materials for interesterification have a water content of 0.01 to 0.2 wt. % and a residence time in the reaction column is 2 hours or shorter on the average.

12. A process as claimed in claim 9, in which the lipolytic enzyme is adsorbed and immobilized on the insoluble carrier containing said fatty acid or derivative thereof in an aqueous medium.

13. A process as claimed in claim 9, in which said fatty acid or derivative thereof is ricinoleic acid.

* * * * *

UNITED STATES PATENT AND TRADEMARK OFFICE
CERTIFICATE OF CORRECTION

PATENT NO. : 5 128 251

DATED : July 7, 1992

INVENTOR(S) : Hideki YOKOMICHI et al

It is certified that error appears in the above-identified patent and that said Letters Patent is hereby corrected as shown below:

Column 26, lines 3-4; change "aluric" to ---lauric---.

Signed and Sealed this

Sixteenth Day of November, 1993

Attest:

BRUCE LEHMAN

Attesting Officer

Commissioner of Patents and Trademarks